(12) United States Patent
Ahlgren

(10) Patent No.: US 6,852,126 B2
(45) Date of Patent: Feb. 8, 2005

(54) STACKABLE INTERLOCKING INTERVERTEBRAL SUPPORT SYSTEM

(75) Inventor: Dan K. Ahlgren, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 09/904,179

(22) Filed: Jul. 11, 2001

(65) Prior Publication Data

US 2002/0082693 A1 Jun. 27, 2002

Related U.S. Application Data

(60) Provisional application No. 60/218,975, filed on Jul. 17, 2000.

(51) Int. Cl.[7] .................................................. A61F 2/44
(52) U.S. Cl. ................................................... 623/17.11
(58) Field of Search ........................... 623/17.11, 17.15, 623/17.16; 606/60, 61, 62, 63, 64, 69, 72, 73; 446/69, 106, 108, 117, 120, 124, 128

(56) References Cited

U.S. PATENT DOCUMENTS

| | | | |
|---|---|---|---|
| 5,192,327 A | | 3/1993 | Brantigan |
| 5,484,403 A | * | 1/1996 | Yoakum et al. ................ 604/59 |
| 5,665,122 A | | 9/1997 | Kambin |
| 5,702,455 A | * | 12/1997 | Saggar ..................... 623/17.15 |
| 5,865,848 A | * | 2/1999 | Baker .......................... 623/17 |
| 6,048,342 A | * | 4/2000 | Zucherman et al. .......... 606/61 |
| 6,159,211 A | | 12/2000 | Boriani et al. |
| 6,193,756 B1 | * | 2/2001 | Studer et al. ............ 623/17.15 |
| 6,224,631 B1 | * | 5/2001 | Kohrs ..................... 623/17.11 |
| 6,241,769 B1 | * | 6/2001 | Nicholson et al. ....... 623/17.11 |
| 6,258,125 B1 | * | 7/2001 | Paul et al. ............... 623/17.11 |
| 6,371,989 B1 | * | 4/2002 | Chauvin et al. ......... 623/17.11 |
| 6,454,806 B1 | * | 9/2002 | Cohen et al. ............ 623/17.15 |

\* cited by examiner

Primary Examiner—Eduardo C. Robert
Assistant Examiner—Anuradha Ramana
(74) Attorney, Agent, or Firm—Jonathan Spangler (57) ABSTRACT

A intervertebral support system, comprising: a center portion having top and bottom recesses; a top portion having a bottom recess, the bottom recess in the top portion interlocking with the top recess in the center portion when the top position is positioned on top of the center portion; and a bottom portion having a top recess, the top recess in the bottom position interlocking with the bottom recess in the center portion when the bottom portion is positioned under the center portion.

5 Claims, 15 Drawing Sheets

STACKABLE INTERLOCKING INTERVERTEBRAL SUPPORT SYSTEM

CROSS-REFERENCES TO RELATED APPLICATIONS

This application claims the benefit of prior provisional application No. 60/218,975, filed on Jul. 17, 2000, under 37 CFR §1.78(a)(3), the full disclosure of which is incorporated herein by reference.

BACKGROUND OF THE INVENTION

The present invention provides a stackable interlocking intervertebral support system, and methods for supporting adjacent vertebrae using a stackable interlocking intervertebral support system.

In preferred aspects, the present system comprises two, three (or more) separate portions which are stacked together to form an interlocked intervertebral support assembly. Advantageously, two of these three (or more) portions may be identical in size and shape, as will be explained. In the optional aspect of the invention in which only two separate portions are used, these two portions may be identical to one another in size and shape.

In one preferred aspect, the present invention preferably comprises a center portion, a top portion and a bottom portion. The top portion is positioned on top of the center portion and the bottom portion is positioned under the center portion. The top and bottom portions may be identically shaped and dimensioned, but are positioned upside down with respect to one another, on opposite sides of the center portion, as will be explained.

In one aspect of the invention, however, only two portions are used, with the top portion being positioned directly on top of the bottom portion (with no center portion(s) required).

In further aspects of the present invention, more than three separate portions may be used. In such aspects, a plurality of identically shaped center portions are stacked one on top of the other. In other alternate aspects, various portions (including top, center and bottom portions) may be stacked side by side one another.

In accordance with the present invention, the center portion has a recess in each of its top and bottom surfaces. Each of the top and bottom portions of the present system also have recesses therein which engage and interlock with the recesses in the center portion. More specifically, the top portion preferably has a recess in its bottom surface and the bottom portion has a recess in its top surface which engage the respective recesses in the top and bottom of the center portion.

The present invention is assembled simply by stacking the three portions (top, center & bottom) one on top of one another in a patient's intervertebral space. When stacked together, the present assembly will form an "X" or "cross" type of shape, providing support over a large surface area of the adjacent vertebrae.

In further optional aspects of the invention, more than three portions are stacked together one on top of one another in a patient's intervertebral space. Specifically, a plurality of center portions are stacked on a bottom portion and a top portion is stacked thereover.

A further advantage of the present system is that, when assembled, it provides support in two perpendicular directions, thereby supporting a large area of the adjacent vertebrae, yet using only a minimal amount of material in actually achieving this advantage. This advantage is due, at least in part, to the assembled "cross" shape of the assembly. Moreover, the present invention can be dimensioned to be of a size such that the "arms" of the "cross" extend outwardly towards the edges of the vertebrae, providing support over the cortical bone at the vertebral edges.

Another advantage of the present invention is that, as the adjacent vertebrae tend to push together, this will hold the present support assembly together, even in the absence of any mechanical fastening or securing mechanisms between the top, center & bottom portions of the system. Specifically, both (one or more) center portion(s) and the two top/bottom portions are uniquely shaped and dimensioned such that when positioned one on top of another, they will remain firmly together, resisting any lateral tendency to slip apart.

Yet another advantage of the present invention is that it may be easily inserted into a patient's intervertebral space in a bi-portal minimally invasive surgical approach. Specifically, the bottom portion may be inserted through a first cannula into the patient's intervertebral space, with the center portion(s) thereafter being inserted through a second cannula into the patient's intervertebral space. The top portion may then be inserted through the first cannula into the patient's intervertebral space. In this aspect of the invention, the first and second cannula are generally perpendicular to one another, being positioned in opposite posterolateral approaches.

Alternatively, all of the portions of the assembly may be inserted through the same operating cannula into the patient's intervertebral space, with successive portions then rotated perpendicular to one another after they have been positioned in the patient's intervertebral space.

In preferred aspects, each of the center, top and bottom portions of the assembly have a tapered end, which is dimensioned to engage a ramping structure disposed within one of the recesses on an adjacent portion such that the separate portions of the assembly may be "slip-fit" together, with pressure between the adjacent vertebrae holding each of the pieces of the assembly together.

In addition, an optional tapered front end of the center portion may used to pry apart the adjacent vertebrae, prior to positioning the top portion thereover.

In optional aspects of the invention, a plurality of the present support assemblies can be positioned in a patient's intervertebral space, either on top of, beside, or both on top of and beside, one another.

DETAILED DESCRIPTION OF THE INVENTION

Figure 1:
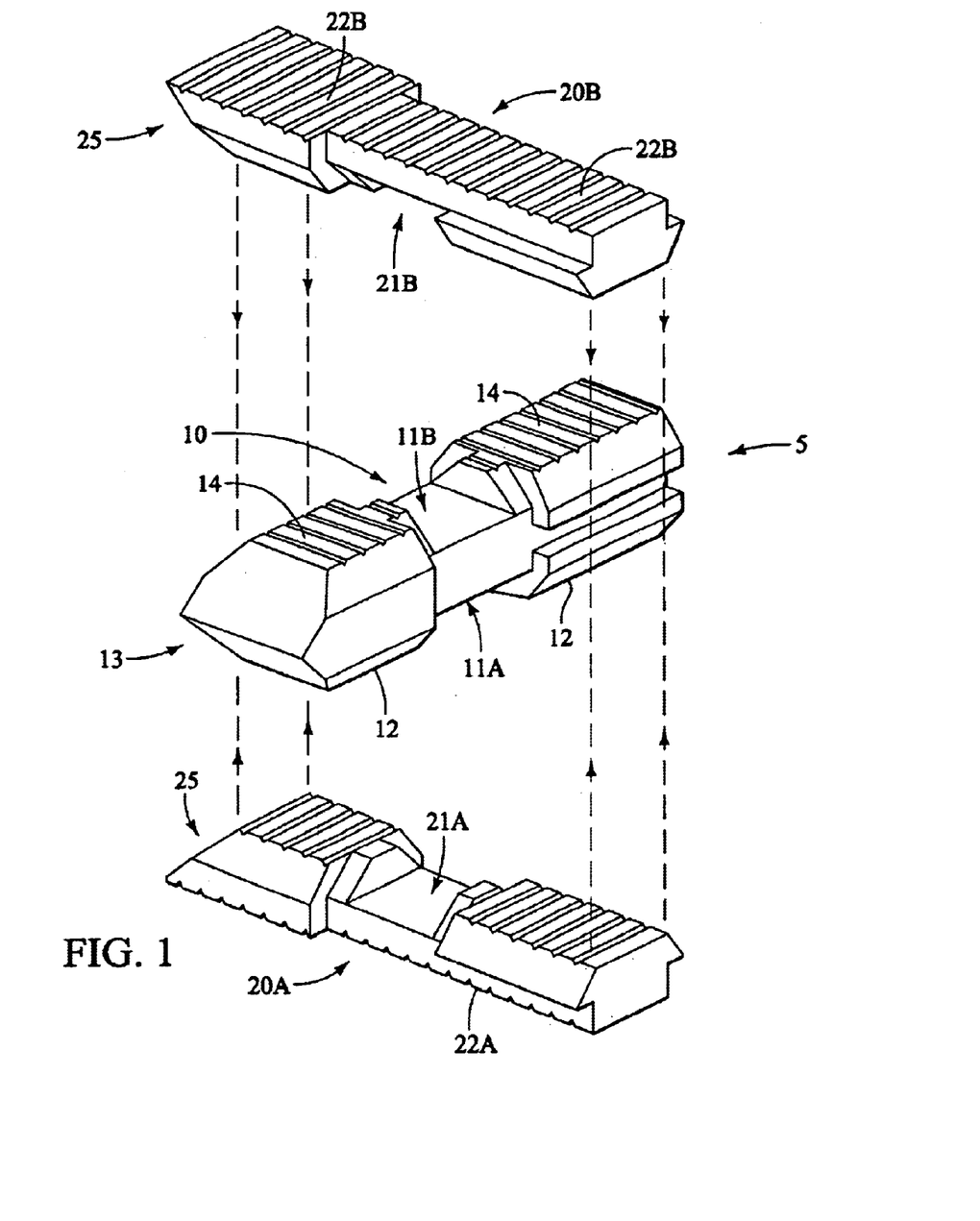
FIG. 1 is an exploded front/side perspective view of an exemplary arrangement of the present stackable interlocking intervertebral support system.

Referring first to FIG. 1, an exploded front side perspective view of the present stackable interlocking intervertebral support system 5 is provided. In one preferred arrangement, system 5 comprises a center portion 10, a bottom portion 20A and a top portion 20B. (As will be explained, other arrangements are possible). As can be seen throughout the attached FIGS., portions 20A and 20B may preferably be identical in shape and size.

Accordingly, the present system 5 may actually comprise one center portion 10 and two top/bottom portions 20.

Figure 2:
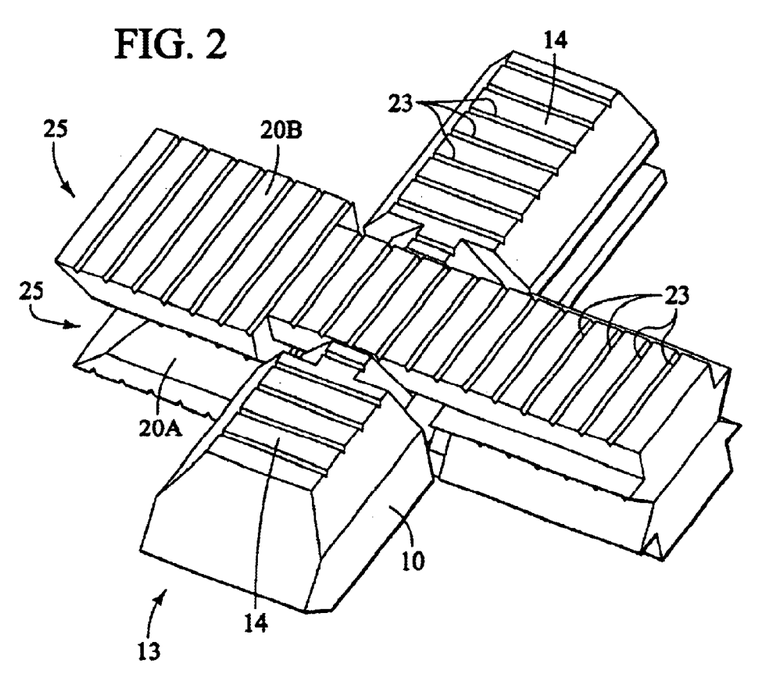
FIG. 2 is a top front/side perspective view of the exemplary arrangement of the present system seen in FIG. 1.
Figure 3:
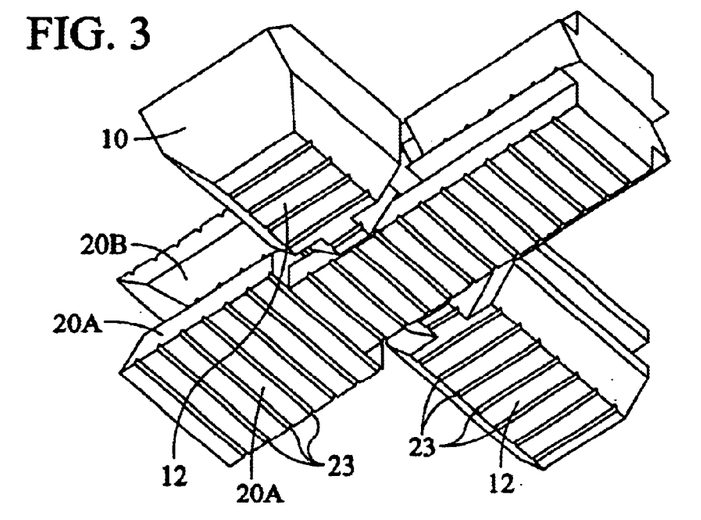
FIG. 3 is a bottom front/side perspective view of the exemplary arrangement of the present system seen in FIG. 1.
Figure 4:
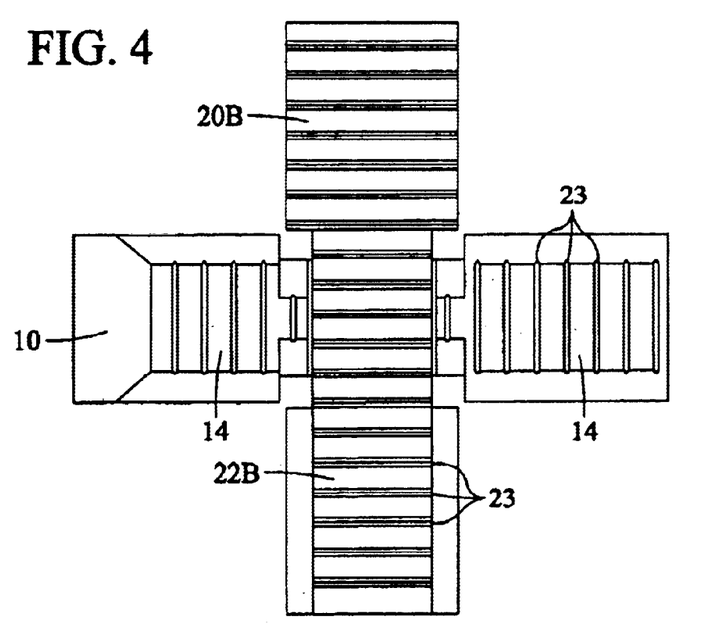
FIG. 4 is a top plan view of the exemplary arrangement of the present system seen in FIG. 1.

FIGS. 2 and 3 show respective top and bottom perspective views of the present system, in an assembled format. As will be explained, an advantage of the present system is that it provides support between adjacent vertebrae without requiring any mechanical fastening systems between the top, center and bottom portions of the assembly. Rather, center portion 10, bottom portion 20A and top portion 20B are all assembled together with their novel shapes assisting in keeping them together.

Referring to the attached Figs., (and to FIGS. 7A to 10 in particular), center portion 10 is provided with bottom recess 11A and top recess 11B, passing thereacross, as shown.

Also referring to the attached Figs., (and to FIGS. 13 to 16 particular), bottom portion 20A is also provided with a top recess 21A. (conversely, being indenxally shaped to bottom portion 20A, top portion 20B is also provided with a bottom recess 21B).

An important aspect of the present invention is that, when bottom portion 20A is positioned below center portion 10, recess 21A will engage and interlock with recess 11A. Conversely, when top position 20B is positioned on top of center portion 10, recess 21B will engage and interlock with recess 11B. Accordingly, when center portion 10, bottom portion 20A and top portion 20B are stacked together, recesses 11 will engage recesses 21, such that assembly 5 forms an "X" or "cross" shape.

As can be seen, recesses 11 and 21 are preferably positioned mid-way (ie: centrally) along the respective lengths of portions 10 and 20. As illustrated, assembly 5 will have an "X" shape with each of the four branches of the "X" being relatively equal in length. Within the scope of the present invention, however, recesses 11 and 21 may instead be positioned closer to one end of their respective portions than another, such that the "X" shape of the present assembly will instead have two of its branches longer than another two of its branches (and may even approach a "V" shape assembly).

Figure 9A:
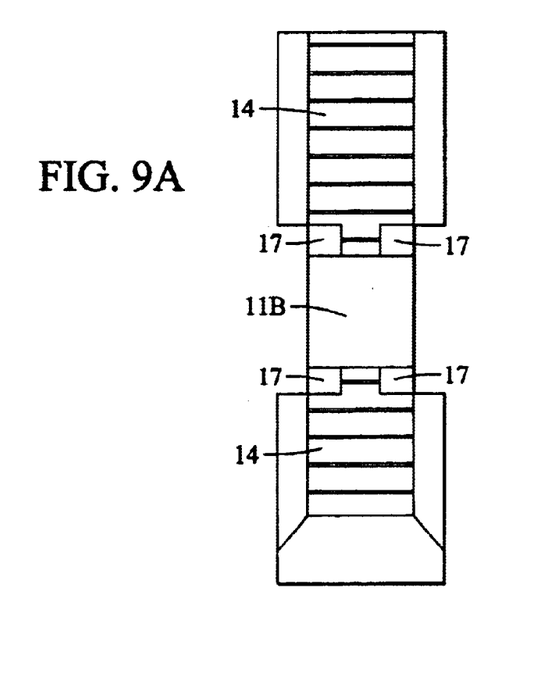
FIG. 9A is a top plan view of the center portion of the present system.
Figure 9B:
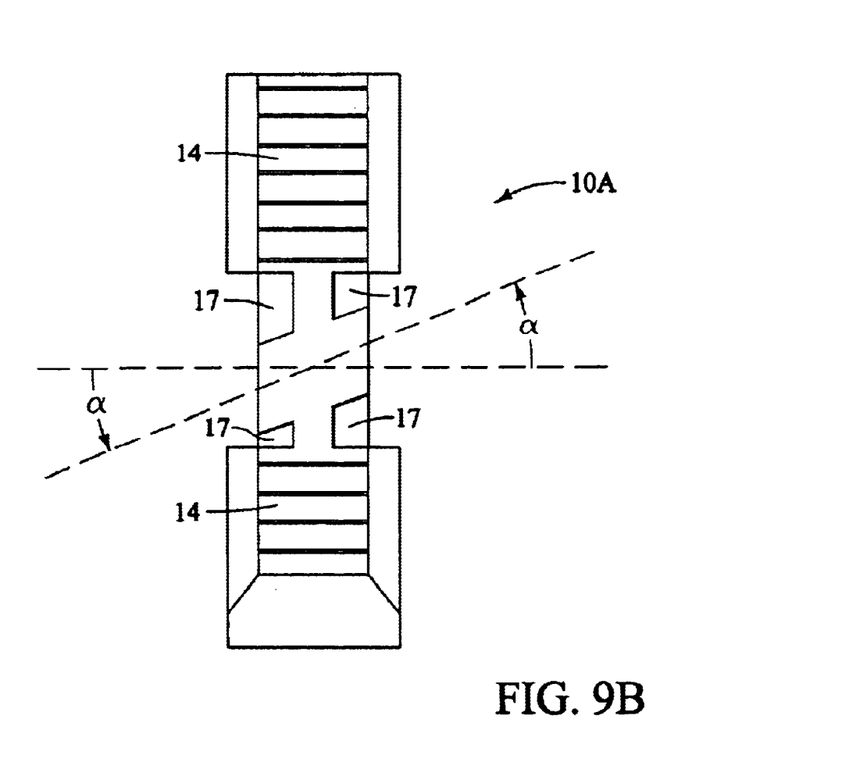
FIG. 9B corresponds to FIG. 9A, but has center ramp/recesses angled to a lateral axis across the center portion.
Figure 10:
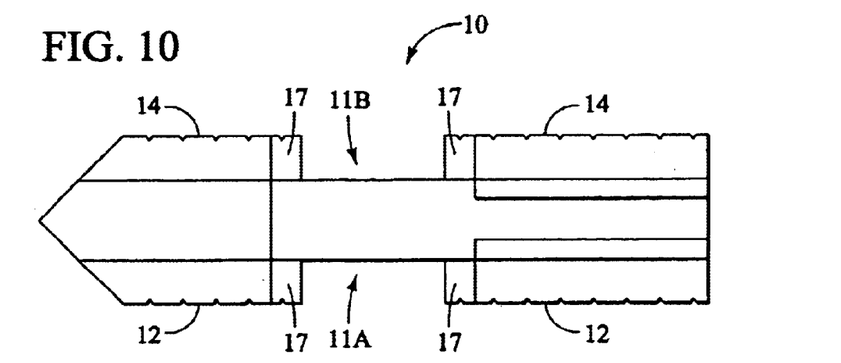
FIG. 10 is a side elevation view of the center portion of the present system.
Figure 11:
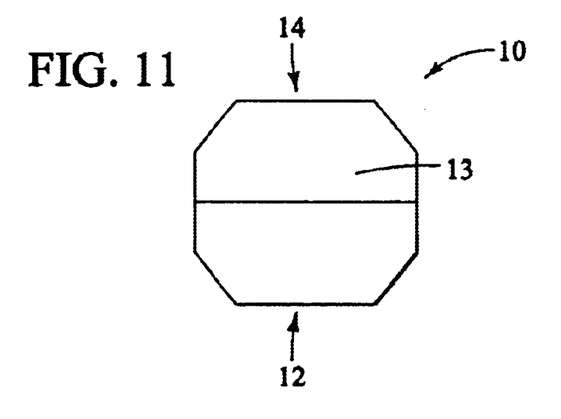
FIG. 11 is a front elevation view of the center portion of the present system.
Figure 12:
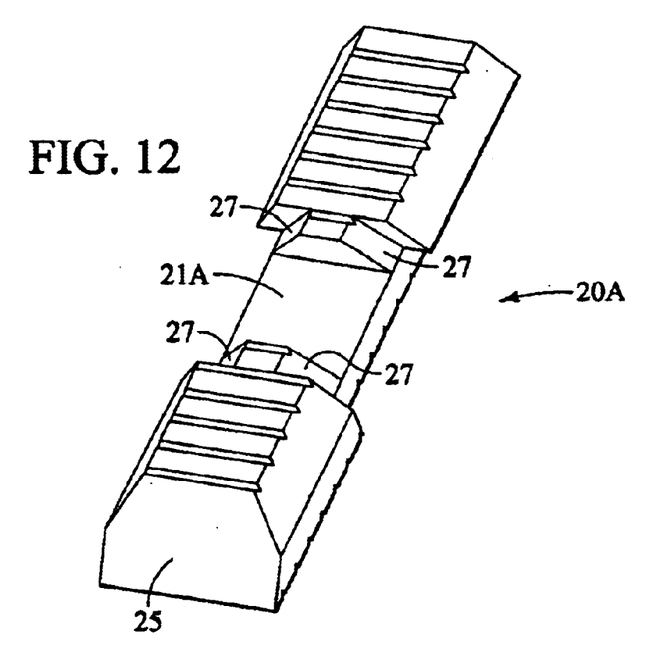
FIG. 12 is a top front perspective view of the bottom portion of the present system, (or is a bottom perspective view of the top portion of the present system).

Moreover, the angles at which recesses 11 and 21 cut laterally across portions 10 and 20 can be angled a as denoted by angle "ALPHA" in FIG. 9B (for center portion 10). As such, when stacked together, the angles between each of the 4 "arms" of the "X" of the present assembly need not be perpendicular to one another. (For example, 2 pairs of arms may be 60° apart, with the other 2 pairs of arms being 120° apart).

As can be seen throughout the attached Figs., center portion 10 has a bottom surface 12 and a top surface 14. Bottom portion 20A has a bottom surface 22A, and top portion 20B has a top surface 22B. When the three portions of the present assembly are assembled, surface 14 is coplanar with surface 22B and surface 12 is coplanar with surface 22A.

Figure 5:
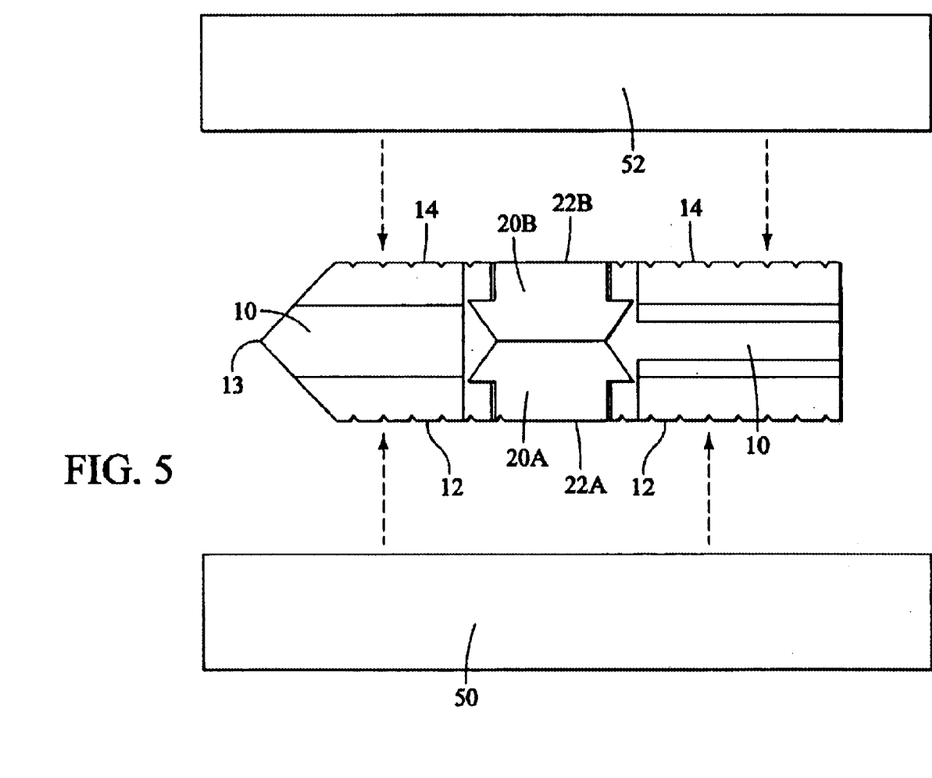
FIG. 5 is a front/side elevation view of the exemplary arrangement of the present system seen in FIG. 1, (show in two adjacent vertebrae in an exploded view).
Figure 6:
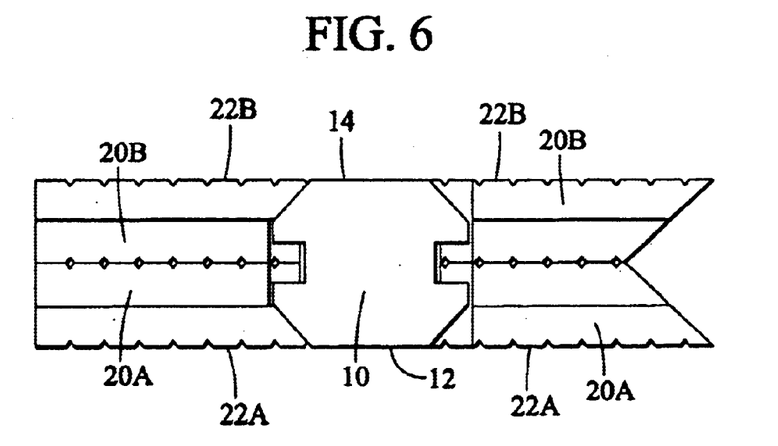
FIG. 6 is a rear elevation view of the exemplary arrangement of the present system seen in FIG. 1.

As shown in FIG. 5, surfaces 12 and 22A together support (ie: buttress against) vertebra 50 and surfaces 14 and 22B together support (ie: buttress against) an opposite adjacent vertebra 52. (For illustration purposes only, opposite adjacent vertebrae 50 and 52 are shown in an exploded view). It is to be understood that after distraction vertebrae 50 and 52 will tend to move toward one another, applying pressure to the top and bottom of assembly 5, keeping assembly 5 together.

As can also be seen, surfaces 12, 14, 22A and 22B may all have a plurality of small grooves 23 (or other surface irregularities) which increases sliding friction across these surfaces.

Figure 18:
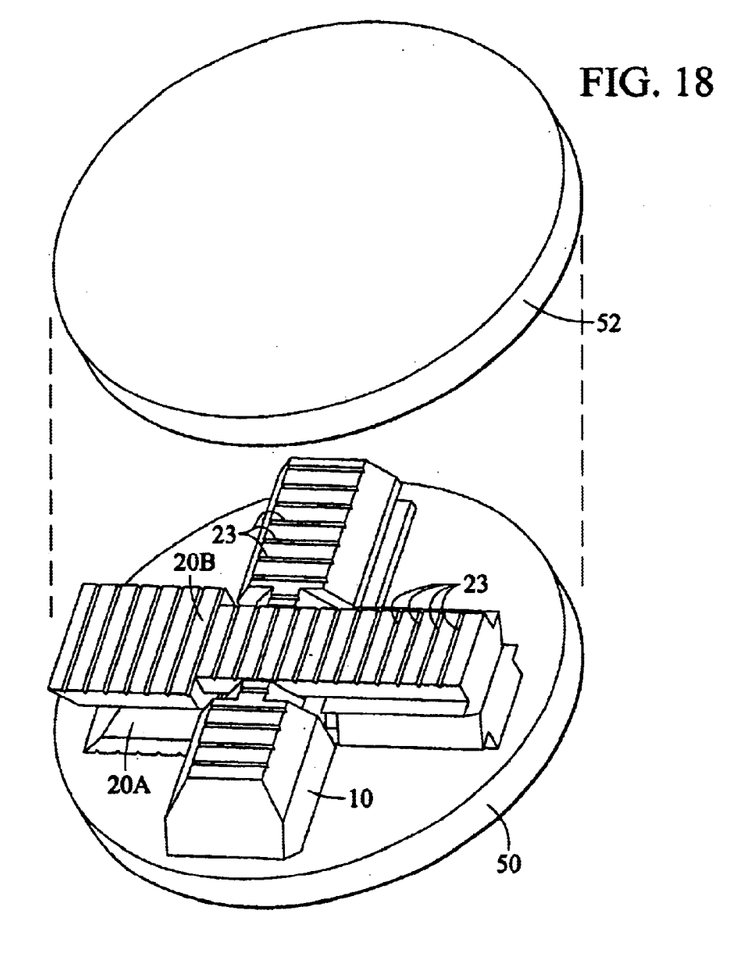
FIG. 18 is a top perspective view of a patient's intervertebral space showing the positioning of the present system (with one vertebrae shown in phantom).
Figure 19:
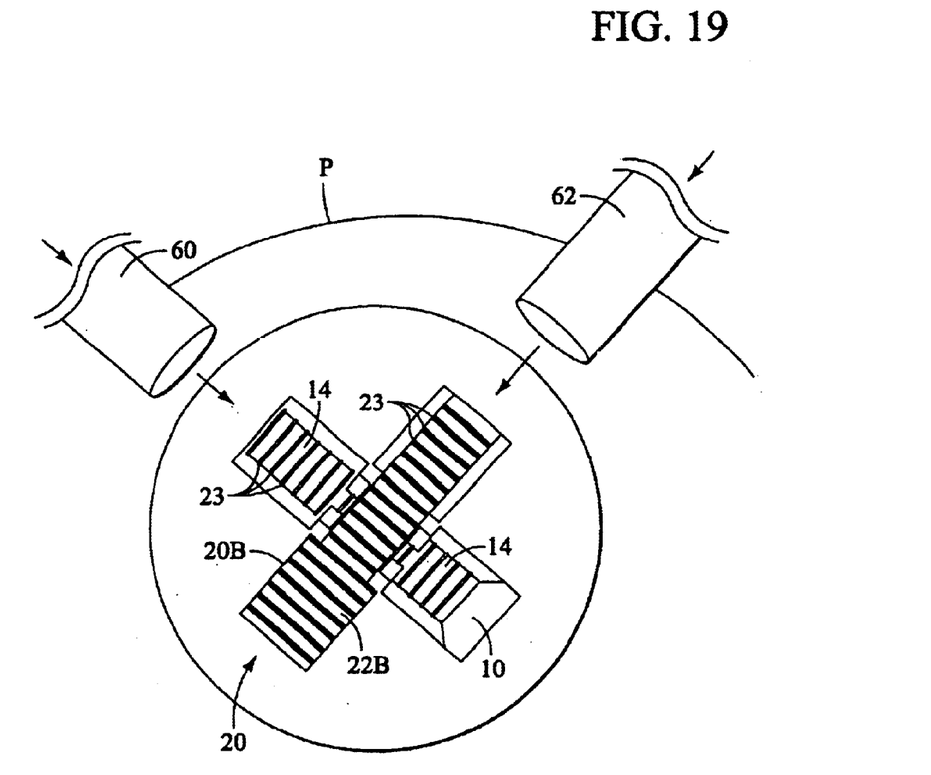
FIG. 19 is a top plan view of a patient's intervertebral space showing posterolateral approaches used in positioning the separate portions of the present system.

A further advantage of the novel shape of center portion 10 is that it has a tapered front end 13. In a preferred method of assembling the present support assembly 5, as illustrated in FIGS. 18 and 19, center portion 10 is advanced minimally invasively into patient P in a posterolateral approach through cannula 60 and positioned between opposite adjacent vertebrae 50 and 52 (shown here as being on top of vertebra 50). Tapered end 13 will tend to pry apart adjacent vertebrae 50 and 52, providing the surgeon with a "self-distracting" vertebral support system. Bottom portions 20A and top portions 20B are advanced through minimally invasive cannula 62 in an opposite posterolateral approach. Typically, bottom portion 20A is positioned first, followed by center portion 10 and top portion 20B stacked sequentially thereover.

Each of center portion 10 and top portion 20B also have tapered front ends 13 and 25 which (as center portion 10 and top portion 20B are sequentially slipped over bottom portion 10 and center portion 10), will engage ramp structures 17 disposed within recesses 21A and 11A in respective bottom portion 20A and center portion 10, such that center portion 10 and top portion 20B are "snap-fitted" over bottom portion 20A.

More specifically, during insertion, vertebrae 50 and 52 will tend to rest against surfaces 12 and 14 of center portion 10. As center portion(s) 10 and top portion 20B are "snap-fitted" over bottom portion 20A and center portion 10, their respective tapered ends 13 and 25 will assist in urging vertebrae 50 and 52 apart.

When assembled, ramp structures 27 disposed within recesses 21A and 21B will interlock with engage ramp structures 17 in center portion 10, such that assembly 5 will be held together, by intervertebral pressure (on surfaces 14 and 22B, and surfaces 12 and 22A) urging vertebrae 50 and 52 together.

Portions 10 and 20 of the present invention may preferably each have a narrow elongated shape, as shown. Accordingly, they may be dimensioned to be small enough to pass through an operating cannula, for example, an operating cannula having an interior diameter equal to, or less than, 8 mm or 6 mm.

In preferred aspects of the invention, portions 10 and 20 are preferably made of bone allograft material, offering the advantages of promoting healing and eventual absorption of system 5. Alternatively, portions 10 and 20 may be made of metal, or any other suitable bio-implantable material.

Figure 7A:
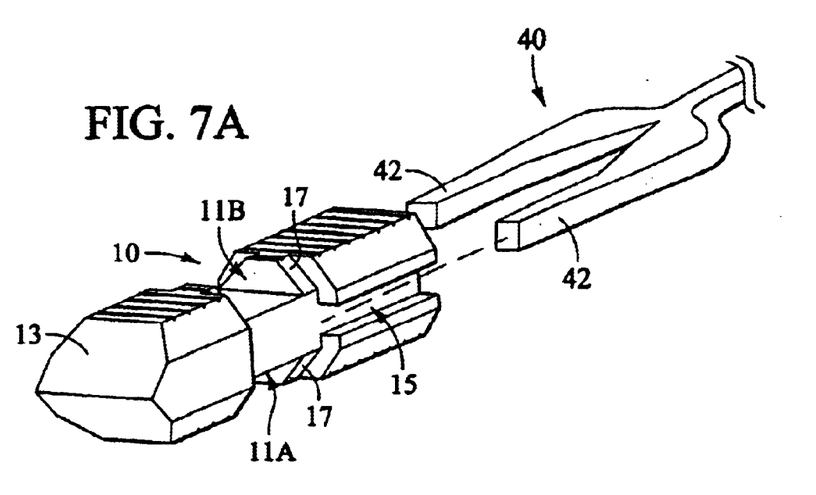
FIGS. 7A, 7B and 7C are front perspective views of the center portion of the present system.
Figure 7B:
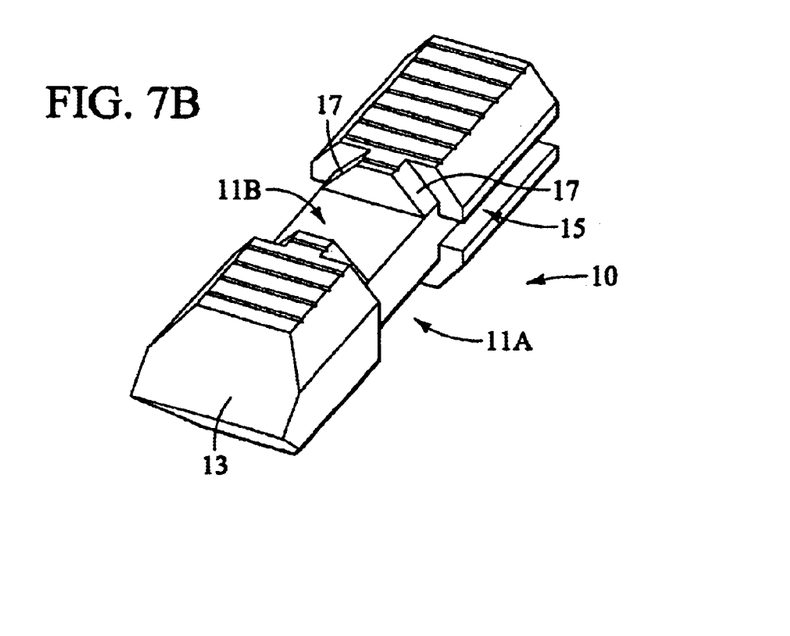
Figure 7C:
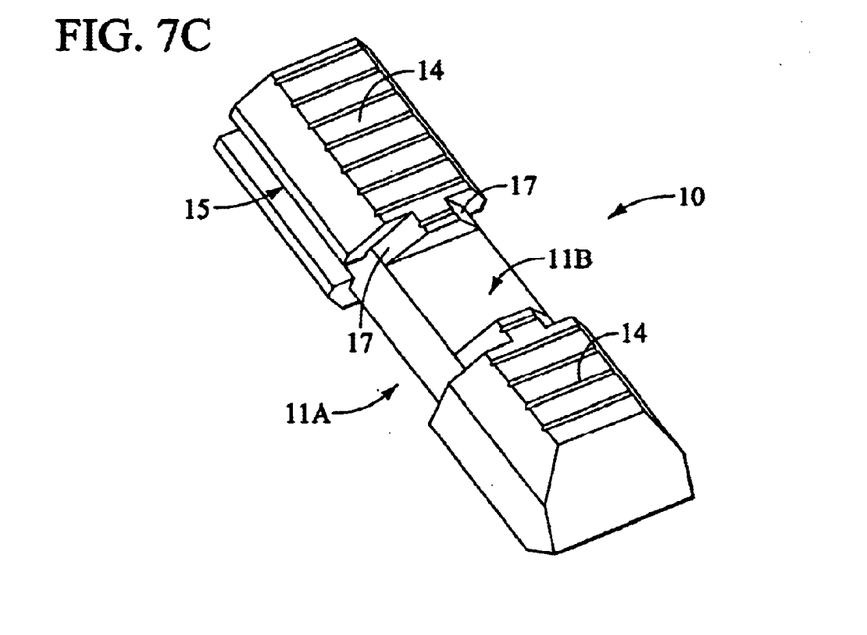
Figure 8:
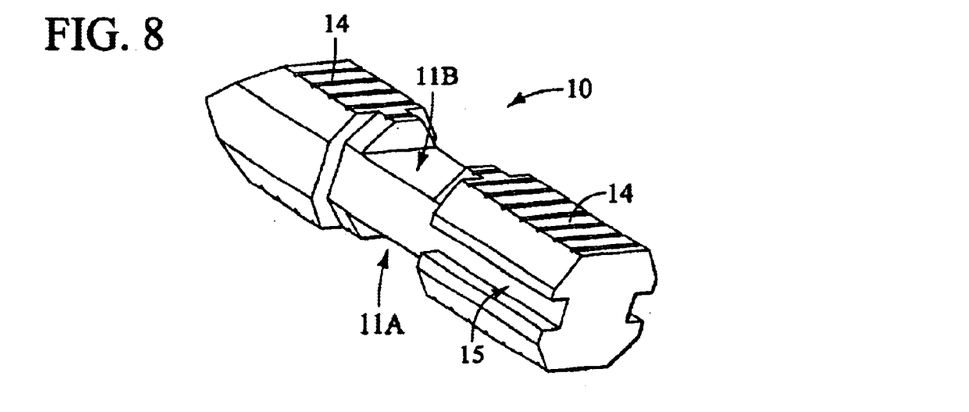
FIG. 8 is a rear perspective view of the center portion of the present system.
Figure 13:
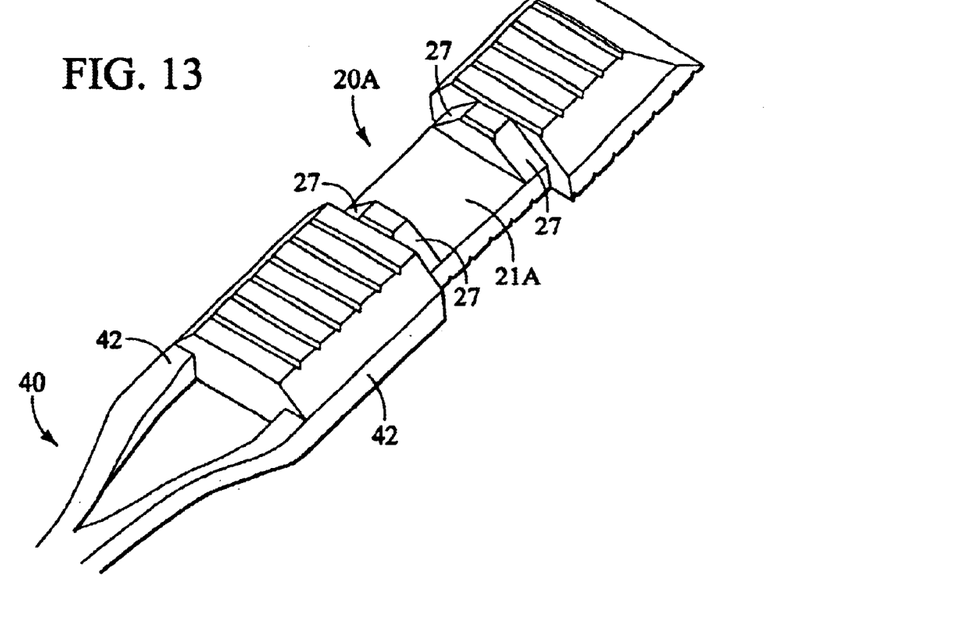
FIG. 13 is a top rear perspective view of the bottom portion of the present system, (or is a bottom perspective view of the top portion of the present system).
Figure 14:
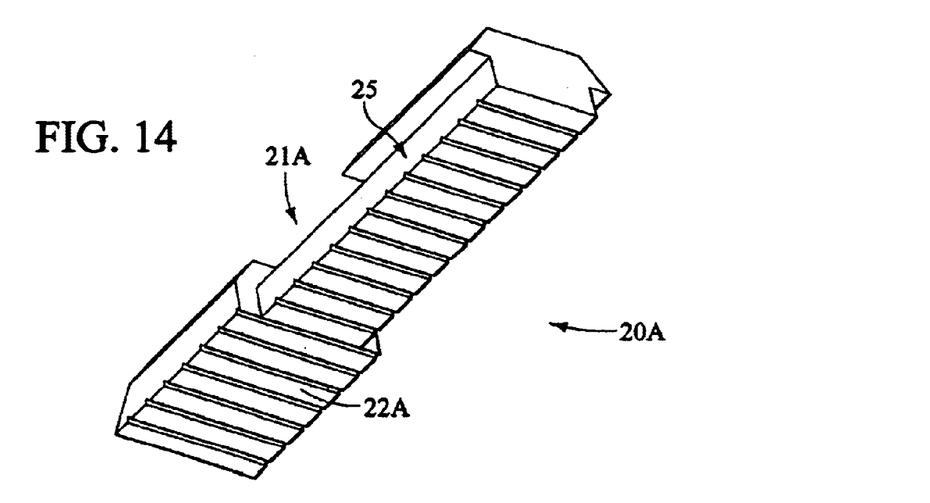
FIG. 14 is a bottom rear perspective view of the bottom portion of the present system.
Figure 15:
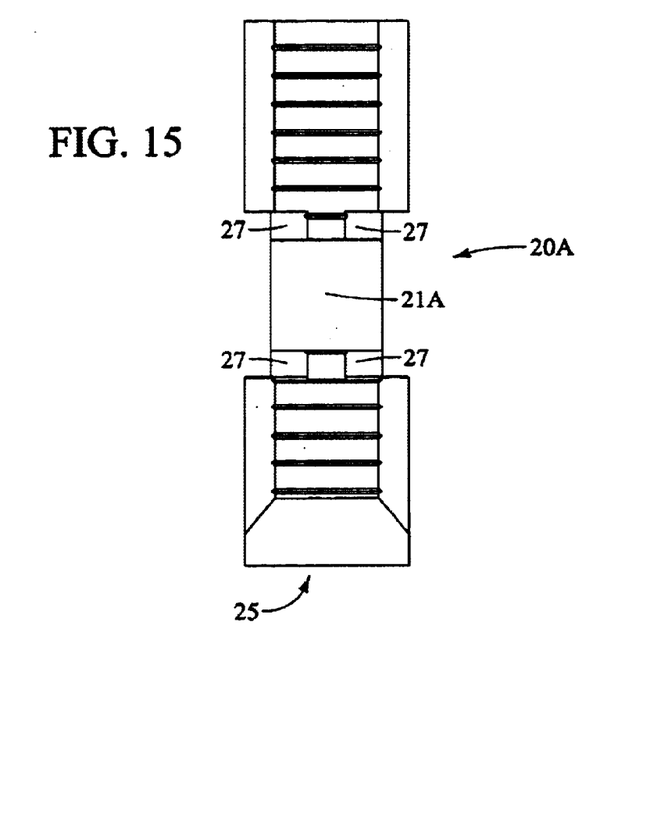
FIG. 15 is a top plan view of a bottom portion of the present system.
Figure 16:
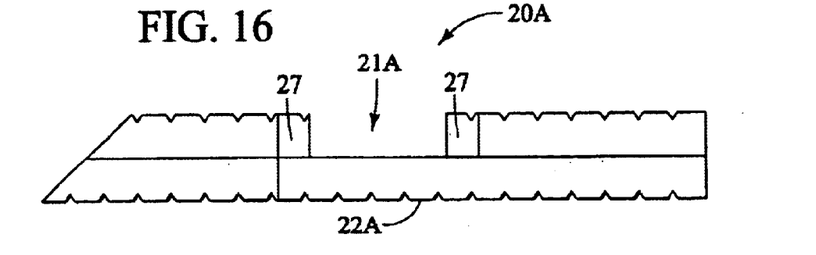
FIG. 16 is a side elevation view of the bottom portion of the present invention.
Figure 17:
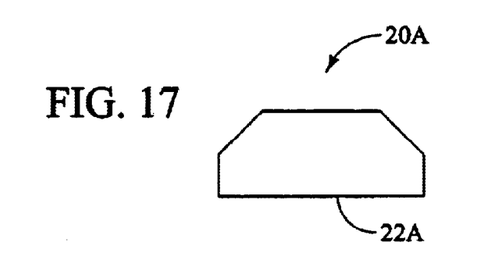
FIG. 17 is a front elevation view of the bottom portion of the present invention.

Each of center portion 10, and top/bottom portion 20 may optionally have side grooves 15 and 25 in which opposite prongs 42 of a two prong inserter 40 (such as a "pinching" inserter as shown in FIGS. 7A and 13) which may be used when inserting each of center portion 10 and top/bottom portions 20 through respective surgical cannula 60 and 62.

Figure 20:
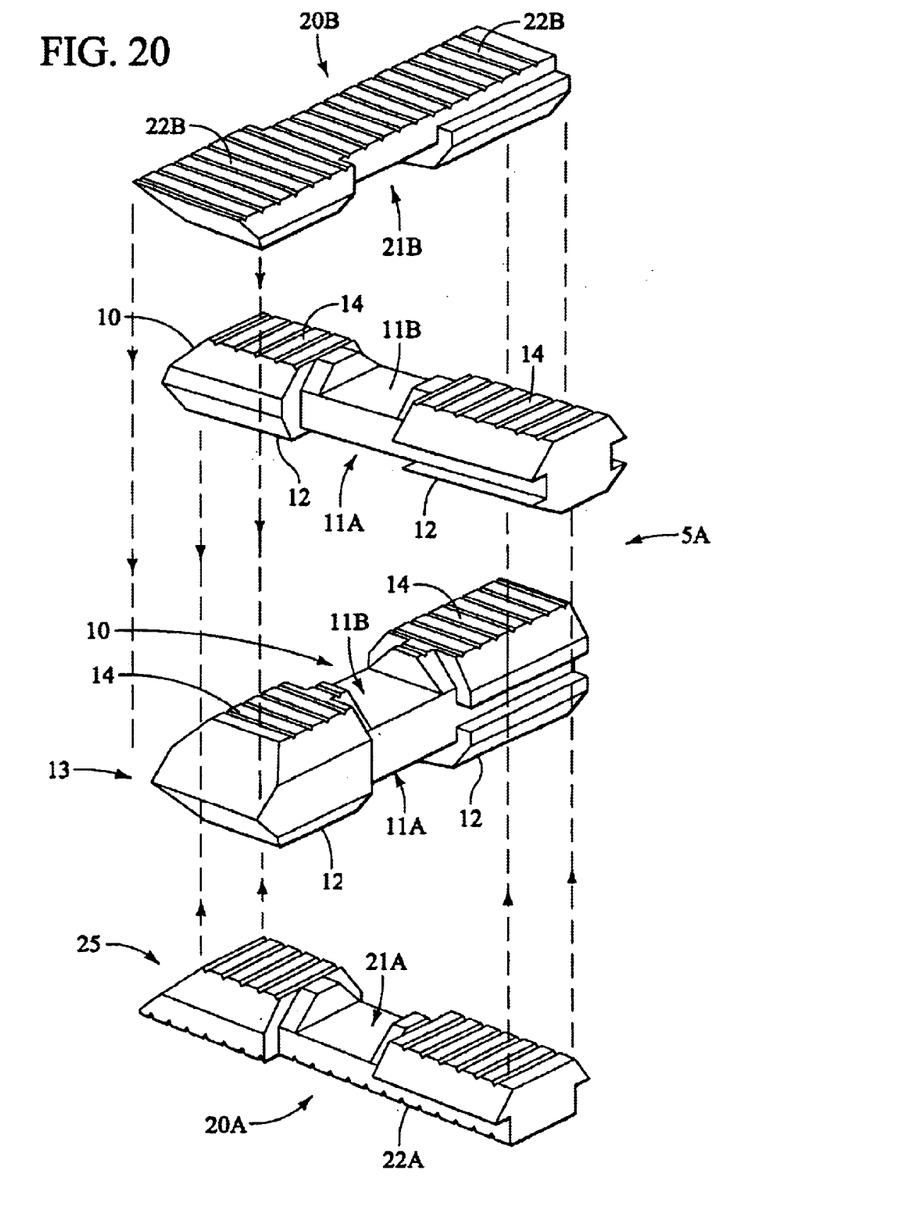
FIG. 20 is an exploded perspective view of a patient's intervertebral space showing an assembly comprising four portions, (including two center portions, a top portion and a bottom portion) positioned one on top of the other.

If desired, the vertical height of the present system can be increased by stacking more than one center portion 10 (as shown in FIG. 20 in which an assembly 5A is shown having two center portions 10). It is to be understood that more than two center portions 10 may be used in assembling the present intervertebral support system, as desired.

In yet another optional aspect of the invention, assemblies 5 may be made small enough such than more than one can be positioned side by side in a patient's intervertebral space.

Figure 21:
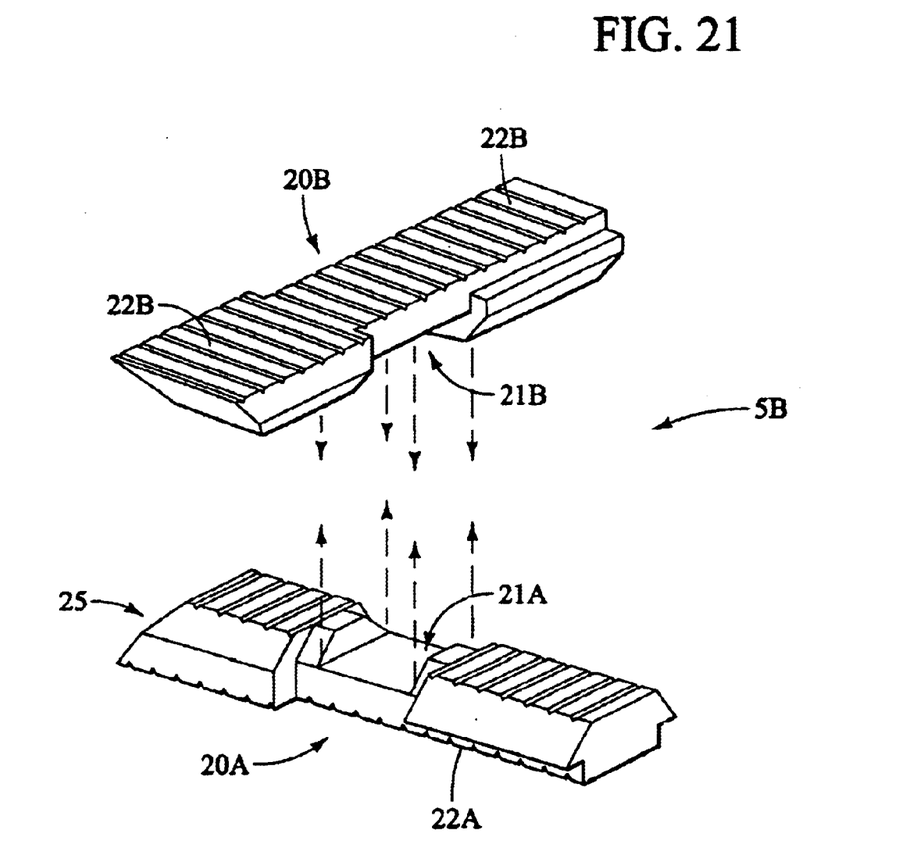
FIG. 21 is an exploded perspective view of a two portion intervertebral support assembly.

As is seen in FIG. 21, a two portion intervertebral support assembly 5B is also contemplated. In this aspect of the invention, top portion 20B is positioned directly on top of bottom portion 20A, with recesses 21A and 21B interlocking together.

Many other system arrangements are possible. For example, two, or more than two portions 10 can be stacked on top of one another (similar to the stacking of portions 20 in FIG. 21).

What is claimed is:

1. An intervertebral support system, comprising:
   a center portion dimensioned to be positioned in an intervertebral space, said center portion having a generally flat top surface, a generally flat bottom surface, a top recess formed in the top flat surface facing generally cranially when the center portion is positioned within the intervertebral space, and a bottom recess formed in the bottom flat surface facing generally caudally when the center portion is positioned within the intervertebral space;
   a top portion having a generally flat top surface and a bottom recess facing generally caudally which interlocks with the top recess in the center portion when the top portion is positioned on top of the center portion within the intervertebral space; and
   a bottom portion having a generally flat bottom surface and a top recess facing generally cranially which interlocks with the bottom recess in the center portion when the center portion is positioned on top of the bottom portion within the intervertebral space,
   wherein the top surface in the center portion and the top portion are generally co-planar when the top portion is positioned on top of the center portion, and wherein the bottom flat surfaces of the center portion and bottom portion are generally co-planar when the bottom portion is positioned under the center portion.

2. The intervertebral support system of claim 1, wherein the top and bottom surfaces have a plurality of small grooves formed therein, the grooves increasing sliding friction across the top and bottom surfaces.

3. The intervertebral support system, comprising:
   a center portion having top and bottom recesses;
   a top portion having a bottom recess, the bottom recess in the top portion interlocking with the top recess in the center portion when the top portion is positioned on top of the center portion; and
   a bottom portion having a top recess, the recess in the bottom position interlocking with the bottom recess in the center portion when the center portion is positioned on top of the bottom portion, wherein the top and bottom portions are positioned parallel to one another and perpendicular to the center portion when the top portion is positioned on top of the center portion and the bottom portion is positioned under the center portion.

4. A method of supporting adjacent vertebrae, by assembling an intervertebral support assembly between adjacent vertebrae comprising:
   advavcing a bottom portion having a top recess into a patient's intervertebral space;
   advancing a center portion having top and bottom recesses into patient's intervertebral space; and
   advancing a top portion into the patient's intervertebral space; wherein the top portion has a bottom recess which interlocks with the top bottom recess in the center portion, and the bottom portion has a stop recess which interlocks with the bottom recess in the center portion such that a top surface of the top portion is generally coplanar with top surface of the center portion, and such that a bottom surface on the bottom portion is generally coplanar with bottom surface of the center portion, wherein the bottom portion and the top portion are advanced in a first posterolateral approach and the center portion is advanced in a second posterolateral approach, wherein the first posterolateral approach is generally perpendicular to the second posterolateral approach.

5. A method of supporting adjacent vertebrae, by assembling an intervertebral support assembly between adjacent vertebrae, comprising:
   advancing a bottom portion having a top recess into a patient's intervertebral space;
   advancing a center portion having a bottom recess into patient's intervertebral space; and
   advancing a top portion into the patient's intervertebral space, wherein the portion has a bottom recess which interlock with the top bottom recess in the center portion and the bottom portion has a top races which interlocks with the bottom recess in the center portion such that a top surface of the top portion is generally coplanar with the top surface of the center portion, and such that a bottom surface of the bottom portion is generally coplanar with the bottom surface of the center portion, wherein the intervertebral support assembly has an X-shape.

* * * * *